ically-sealed fumigant container having a can enclosing a smoke-generating mixture and an internal heater formed of auto-combustible material for activating the mixture to produce an exothermic reaction resulting in smoke which disperses pesticidal agents into the atmosphere of the area being fumigated. The mixture preferably has an ammonium nitrate and dicyandiamide base and a silica additive which acts to regulate the exothermic reaction whereby the reaction proceeds at a substantially constant rate.

United States Patent
Radulescu

[11] 3,956,849
[45] May 18, 1976

[54] FUMIGANT CONTAINER

[76] Inventor: Tudor Radulescu, c/o Laboratoire de Chimie et de Biologie, 71 Lenozan, La Salle, France

[22] Filed: Aug. 16, 1974

[21] Appl. No.: 498,136

[30] Foreign Application Priority Data

Aug. 27, 1973 France ............................. 73.31007
Feb. 13, 1974 France ............................. 74.04811

[52] U.S. Cl. .................................... 43/127; 424/42
[51] Int. Cl.² .......................................... A01M 13/00
[58] Field of Search ...................... 43/127, 129, 125; 21/110, 111; 424/42

[56] References Cited
UNITED STATES PATENTS

| | | | |
|---|---|---|---|
| 1,222,883 | 4/1917 | Meek .................................... | 424/42 |
| 1,856,062 | 4/1932 | Houghton ............................. | 43/127 |
| 2,557,815 | 6/1951 | Wheelwright et al. ................ | 43/127 |
| 2,700,011 | 1/1955 | Taylor .................................. | 424/42 |
| 2,707,695 | 5/1955 | Courtier ............................... | 424/42 |

FOREIGN PATENTS OR APPLICATIONS

| | | | |
|---|---|---|---|
| 498,286 | 12/1953 | Canada ................................ | 43/129 |
| 768,342 | 5/1934 | France ................................. | 21/111 |

*Primary Examiner*—Warner H. Camp

[57] ABSTRACT

A hermetically-sealed fumigant container having a can enclosing a smoke-generating mixture and an internal heater formed of auto-combustible material for activating the mixture to produce an exothermic reaction resulting in smoke which disperses pesticidal agents into the atmosphere of the area being fumigated. The mixture preferably has an ammonium nitrate and dicyandiamide base and a silica additive which acts to regulate the exothermic reaction whereby the reaction proceeds at a substantially constant rate.

2 Claims, 3 Drawing Figures

FUMIGANT CONTAINER

BACKGROUND OF THE INVENTION

This invention relates generally to generators for producing smoke to disperse fungicidal, insecticidal, bactericidal and other disinfecting and sterilizing agents, and more particularly to a sealed container having both a smoke-generating pesticidal mixture and an internal heater therein for activating the mixture.

The term pesticide is now officially used to cover all toxic chemicals capable of destroying or inhibiting the activity of plant or animal pests. This term therefore encompasses insecticides, herbicides, fungicides, rodenticides and other disinfecting or sterilizing agents.

It is well known that the most effective treatment for predators encountered in the manufacturing and storage facilities of the food industry as well as in the transportation of perishables, involves the dispersion into the atmosphere of vapors containing minute particles of active pesticidal agents. Due to their very light weight, these particles float in the air and make contact with the contaminants being treated.

Commonly used for this purpose is a smoke-producing mixture having a base of ammonium nitrate and dicyandiamide. Once the mixture is heated to the proper temperature, an exothermic reaction occurs, which action is then independent of the heat source. It is therefore necessary to provide a heat source capable of converting the mixture into smoke. This conversion poses problems which heretofore have not been solved in a satisfactory manner.

Among the various techniques hitherto employed for heating the smoke-generating mixture are electric and open-flame or gas heaters. It is also known, as disclosed in French Pat. No. 1,400,481, to provide a heater in the form of an auto-combustible material molded into a receptacle for containing the gas-generating mixture. The drawback to this approach is that during prolonged storage, the mixture diffuses into the auto-combustible material of the receptacle. To overcome this drawback, French Pat. No. 1,439,921 discloses an arrangement in which the smoke-generating mixture is contained within a thin-walled metal can, the can being nested within the receptacle formed of auto-combustible material.

In the case of an electric heater or of a auto-combustible receptacle adapted to heat a metal can having a smoke-generating mixture therein, the heat source is exterior to the can and the heat must be transmitted from the exterior to the interior of the can. As a consequence, a substantial portion of the available heat is dissipated into the ambient atmosphere by radiation and convection, the remaining portion being conducted to the active mixture within the can container.

Moreover, with a receptacle made of auto-combustible material surrounding the metal can, despite the fact that the mass of this material is very large (i.e. — 270 grams), the resultant heating is irregular or erratic. If the smoke-generating mixture is heated too abruptly, the active ingredients therein deteriorate and the insecticidal, bactericidal or fungicidal effectiveness thereof is markedly diminished, whereas if the mixture is insufficiently heated, the emission of smoke is incomplete and a significant quantity of unvolatilized material remains on the bottom of the metal can.

A further objection to the use of receptacles made of auto-combustible material for heating the metal can is that the heating efficiency will vary according to the prevailing climate, the season of the year and the ventilating conditions of the chamber being fumigated. For example the same receptacle which works in a perfectly satisfactory manner a food warehouse situated in the south of France, will perform poorly in a warehouse belonging to the same company but located in the north of France. These irregularities are even more marked in well-ventilated silos situated in North Africa or in the Scandinavian countries.

Still another objection to receptacles formed of combustible material is that it constitutes a fire hazard and its use may require special safety precautions. This factor has militated against the widespread use of such combustible receptacles for heating fumigants.

SUMMARY OF THE INVENTION

In view of the foregoing, the main object of this invention is to provide a hermetically-sealed fumigant container having both a smoke-generating mixture and an internal heater therein for activating the mixture.

A container in accordance with the invention may be used for converting into smoke active ingredients that are effective for the fumigation of industrial and storage chambers, transportation facilities for perishables subject to attack by predators, breeding stables and any other area or facility.

A significant advantage of a container according to the invention is that the heating source for the mixture, instead of being placed outside of the can containing the mixture, is disposed within the can, whereby heat is directly transmitted to the mixture and heat losses due to convection and radiation are eliminated.

Also an object of the invention is to provide a compact fumigant container having an internal heater formed of auto-combustible material whose weight and size are minimal.

Because the smoke-generating mixture and the heater therefor are enclosed in the same container, a substantial reduction in the volume and weight of the fumigant container is effected, as compared to prior arrangements in which the heater is extrinsic to the container. A fumigant container in accordance with the invention make possible a significant reduction in cost price due to savings in raw material. It also diminishes the fall-out of residual pollutants arising from the combustion of the heated material. Furthermore the fact that the heater and the active ingredients are sealed within a moisture-proof container prevents the degradation that otherwise would occur as a result of prolonged storage.

Yet another object of this invention is to provide an improved smoke-generating mixture having an ammonium nitrate and dicyandiamide base, the mixture including a silica additive which acts to regulate the exothermic reaction whereby an excessively violent reaction is avoided, yet the reaction continues by itself at a steady rate until the active ingredients are fully converted into smoke.

Briefly stated those objects are attained in a hermetically-sealed fumigant container having a removable lid, the container having enclosed therein a smoke-generating mixture having an ammonium nitrate and dicyandiamide base and an internal heater formed of auto-combustible material for activating the mixture, whereby when the container is opened and the heater is ignited, a smoke is generated which disperses pesticidal agents into the atmosphere of the area being fumigated.

OUTLINE OF THE DRAWING

For a better understanding of the invention as well as other objects and features thereof, reference is made to the following detailed disclosure, to be read in conjunction with the accompanying drawing, wherein.

DESCRIPTION OF THE INVENTION

Figure 1:
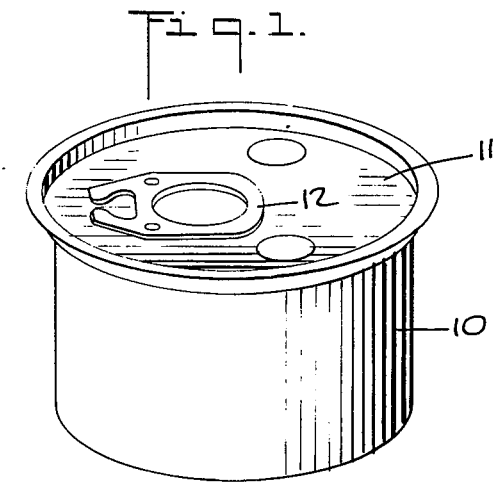
FIG. 1 is a perspective showing of a hermetically sealed fumigant container in accordance with the invention.

Referring now to FIG. 1, there is shown a preferred embodiment of a hermetically-sealed fumigant container in accordance with the invention, the container being shown in the sealed state in which it may be stored indefinitely without deterioration of the active ingredients therein. The container is in the form of a metal can 10 having a removable lid 11. Removal of the lid is effected by means of a pull ring 12. While a cylindrical can is shown, it is to be understood that a can of any other suitable shape may be used.

Figure 2:
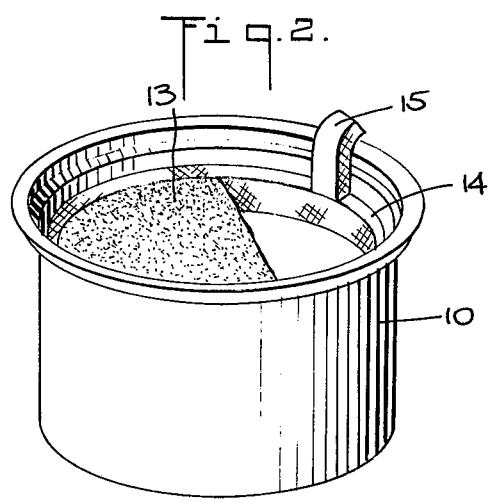
FIG. 2 shows the same container with its lid removed.

FIG. 2 shows the container with the lid removed to expose a charge 13 of a pesticide appropriate to the use for which the smoke generator is intended. In practice, the charge of pesticide may be protectively-sealed within a plastic bag (not shown) which is ruptured before use, the bag being consumed by the heat. The purpose of this bag is to isolate the active powder from the heater during storage.

Installed within can 10 directly against the inner wall thereof is a ring-shaped internal heater 14 provided with an ignition tab 15 that is normally bent over when the lid is closed, but which may be raised, as shown in FIG. 2, before being ignited. Heater ring 14 is formed of auto-combustible material, preferably constituted by cellulosic sheets 4 to 6 millimeters thick, impregnated with a solution of potassium nitrate. The potassium nitrate is sufficiently concentrated so that after drying, the cellulose contains 40 to 60% thereof.

Alternatively, the impregnate may be sodium nitrate (40 to 50%), or barium nitrate (40 to 60%), or cellulose nitrate (10 to 20%). In practice, a thin sheet of aluminum may be interposed between the heater ring and the active powder charge to ensure, in the course of prolonged storage, absolute separation therebetween.

To operate the smoke generator, the tab is ignited by a match or other flame. The ignited tab, in turn, causes the heater ring to burn and to give off the heat necessary to prime and maintain the reaction converting the charge of active ingredients into smoke. Combustion of the heater continues for about 1 to 2 minutes as the heater material is consumed. The heat produced by the internal heater is confined to the can and serves to initiate the exothermic reaction produced by the active mixture. This reaction continues slowly for about 4 to 5 minutes.

The quality and quantity of smoke thus obtained is superior to that resulting from an external heater, the smoke being perfectly white and its yield being 5 to 10% greater. Furthermore, because much less combustible material is used in an internal heater as compared to an external heater in the form of a molded receptacle of auto-combustible material, the resultant emission and fall-out of objectionable dust arising from combustion products are substantially reduced.

For example, a quantity of 100 grams of fungicidal smoke-generating powder converted into smoke by means of an external heater formed by a self-burning paste molded into a receptacle, requires 135 grams of dry, self-burning paste, whereas for the same amount of powder in a container which includes an internal heater in accordance with the invention, requires only 12 grams of self-burning material for this purpose.

Figure 3:
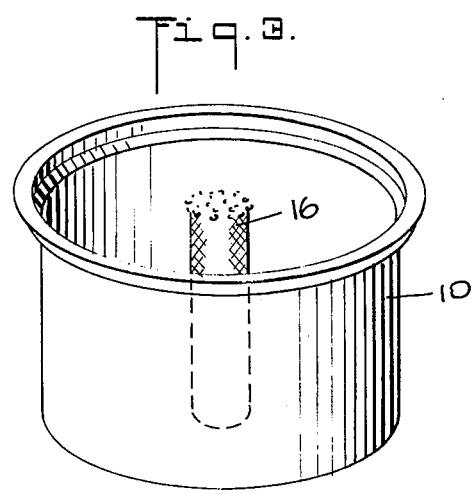
FIG. 3 illustrates another embodiment of the fumigant container.

In the embodment shown in FIG. 3, the internal heater, instead of being in the form of a ring placed against the inner wall of the can, takes the form of a plug 16 placed centrally in the can, the charge of active powder, in this, instance, surrounding the plug. The operation is essentially the same as in the embodiment of FIG. 2, for the heat produced by internal heater is confined within the can and serves to initiate the exothermic reaction of the active powder. In the embodiment shown in FIG. 2, the heat produced by the heater is transmitted from the periphery of the charge of active ingredients inwardly toward the center of the charge whereas in the FIG. 3 embodiment, the direction of heat transmission is reversed.

The shape and height of the self-burning internal heater may be varied in accordance with the interior dimension of the can with a view to producing the amount of caloric units necessary to create and maintain the smoke-generating reaction.

In the following examples, we shall first specify the ingredients which constitute the active powder, and then indicate (A) how many grams of combustible material is required to initiate an exothermic reaction of the powder with an external heater, as compared to (B) the number of grams of material required for this same purpose with an internal heater in accordance with the invention. The relative smoke yield is also specified.

EXAMPLE I

Active Powder: Fungicide powder comprising: silica, ammonium nitrate, dicyandiamide, N. para hydroxy phenyl salicicyl amide. Weight: 200 grams.

A. Heating by external heater requires a weight of dry paste of 270 grams, and the smoke given off weighs 154 grams (yield: 67%).

B. Heating by internal heater necessitates 23 grams of self-burning sheet and disperses 150 grams of smoke (yield:75%).

EXAMPLE II

Active Powder: Fungicide powder comprising: silica, ammonium nitrate, dicyandiamide, sorbic acid. Weight: 200 grams.

A. Heating by external heater necessitates a weight of dry paste of 270 grams, and the smoke given off weighs 114 grams. (yield 57%).

B. Heating by internal heater necessitates 24 grams of self-burning sheet, and disperses 132 grams of smoke (yield: 66%).

EXAMPLE III

Active Powder: Insecticide powder comprising: silica, ammonium nitrate, dicyandiamide, technical malathion and dichlorophos, 23% extract of pyrethrum. Weight: 200 grams.

A. Heating by external heater requires a weight of dry paste of 165 grams, and the smoke given off weighs 178 grams (yield: 89%).

B. Heating by internal heater necessitates 21 grams of self-burning sheet and disperses 185 grams of smoke (yield: 93%).

EXAMPLE IV

Active Powder: Insecticide powder comprising: silica, ammonium nitrate, dicyandiamide, technical malathion and dichlorophos. Weight: 200 grams.

A. Heating by external heater requires a weight of dry paste of 165 grams, and the smoke given off weighs 160 grams (yield: 80%).

B. Heating by internal heater necessitates 21 grams of self-burning sheet and disperses 178 grams (yield: 89%).

EXAMPLE V

Active Powder: Disinfectant powder for breeding, comprising: silica, ammonium nitrate, dicyandiamide, chloramphenicol. Weight: 200 grams.

A. Heating by external heater necessitates a weight of dry paste of 165 grams, and the smoke given off weighs 160 grams (yield: 80%).

B. Heating by internal heater necessitates 25 grams of self-burning sheet and disperses 180 grams of smoke (yield: 90%).

It is to be noted that once an active mixture having an ammonium nitrate and dicyandiamide base is heated to the proper temperature, an exothermic reaction takes place which then becomes independent of the heat applied thereto. But this exothermic reaction is generally much too vigorous, and as a result the active ingredients are decomposed and become less effective. In order to absorb the excessive heat to reduce the violence of the reaction and thereby prevent decomposition of the active ingredients, one may add to the mixture a chemically and biologically inert substance such as kaolin, which is a clay containing aluminum silicate of high purity.

Applicant has discovered however, contrary to expectation, that silica (silicon dioxide), which is biologically and chemically inert, acts as a physical catalyst which functions to accelerate the reaction of the active ingredients to an extent in direct proportion to the amount of silica present. Thus when the proportion of silica is at a maximum (30% by weight of the total mixture), all that is needed to trigger the reaction is a simple match, such as that used for igniting oxy-hydrogen torches. The reaction is then so violent that the whole mass proceeds to bubble.

The violence and the rapidity of the reaction is directly proportional to the amount of silica present in the mixture, so that a decrease of the relative percentage of silica results in a corresponding decrease in the violence and rapidity of the reaction. It has been found that below a minimum percentage by weight of about 4% silica, the reaction is no longer self-sustaining and will stop, while a percentage by weight of about 10% silica represents the optimum amount.

Thus in a smoke-generating pesticidal mixture in accordance with the invention, a preferred composition is one having ammonium nitrate and dicyandiamide in a ratio by weight of about 6 to 4, plus a reaction-regulating agent in the form of silica in a proportion by weight of about 4% to 30%, and preferably 10%, whereby the mixture once it is momentarily heated to initiate the exothermic reaction, thereafter proceeds to react at a substantially constant speed without the addition of heat.

In order to demonstrate the effect of the silica additive, the following experiment was conducted to obtain a comparison between a smoke-generating mixture containing no inert additive, a mixture including kaolin additive and one including a silica additive. Ten grams of each mixture was placed in separate cans in the following proportions:

| Mixture I | Mixture II | Mixture III |
|---|---|---|
| 40% dicyandiamide | 35% dicyandiamide | 35% dicyandiamide |
| 50% ammonium nitrate | 54% ammonium nitrate | 54% ammonium nitrate |
|  | 10% kaolin | 10% silica |

The three can were then simultaneously heated on a single heating plate. It was observed that the reaction began first in the third container, then in the first and finally in the second. The percentage of each mixture converted to smoke was respectively, 80.5 for the third, 78.5 for the first, and 74.2 for the second, thereby indicating that the mixture containing silica produced the greatest output of smoke.

A second experiment was conducted by dispersing in a container such as that illustrated in FIG. 3, 30 grams of mixtures I, II and III. It was observed that with mixture II containing kaolin, it was impossible to initiate the generation of smoke, with mixture I containing no additive the reaction was incomplete, whereas with mixture III containing silica, the reaction was complete. On varying the percentage of silica it was found that a minimum of 4% of silica by weight was necessary to obtain complete fumigation.

As a further experiment, a powder containing 56.4% dicyandiamide; 37.6% ammonium nitrate and 6% driol was prepared. To this powder there was added 10% by weight of Tixosil which is constituted with 92% silica. After stirring to render the mixture homogenous, the powder was deposited to define a strip 1.5 cm thick, 20 cm long and 5 cm wide. One end of this strip was then ignited and the speed of propagation was measured. This measurement yielded the following results:

```
3 minutes-30   mm
4 minutes-48.2 mm
5 minutes-66.8 mm
6 minutes-86.1 mm
```

As will be evident from the above measurement, the rate of propagation represents a fairly uniform progression of 20 mm per minute.

Thus the addition of silica in a proportion of 4% to 30% by weight makes it possible to obtain a reaction which continues by itself without heat from an external source, the reaction taking place at a constant rate.

Instead of a mixture formed by loose powder, the mixture may, by means of a suitable binder, be fabricated into plates or rods also containing sodium chlorate, in which case the rod or plate can be ignited at one end. The rod or plate fumigant is thereafter consumed in a slow and continuous fashion to produce an effective fumigating smoke.

While there has been shown and described preferred embodiments of the invention, it will be appreciated that many modifications may be made therein without departing from the essential spirit of the invention.

I claim:

1. A hermetically-sealed fumigant container comprising:
   A. a non-combustible can having a removable lid,
   B. a smoke generating mixture disposed in said can, said mixture having active ingredients constituted by a loose powder having an ammonium nitrate and dicyandiamide base with a silica additive which when heated for a predetermined period of at least one minute initiates an exothermic reaction generating a pesticidal smoke, said silica additive being in an amount which regulates the exothermic reaction to cause said reaction to proceed at a substantially constant rate, and
   C. an internal heater disposed in said can formed of an auto-combustible material which when the lid is removed and the material is ignited, produces sufficient heat for said predetermined period to initiate said exothermic reaction, said heater being formed of cellulosic material impregnated with an ignition agent selected from the class consisting of potassium nitrate, sodium nitrate and barium nitrate, said heater being in the shape of a ring surrounding said powder mixture and placed against the internal wall of the can, said ring having a fuse extending therefrom.

2. A fumigant container as set forth in claim 1, further including means interposed between said ring and said powder mixture to prevent a chemical reaction therebetween in storage.

* * * * *